(12) United States Patent
Liphardt et al.

(10) Patent No.: US 7,619,752 B2
(45) Date of Patent: Nov. 17, 2009

(54) SAMPLE ORIENTATION SYSTEM AND METHOD

(75) Inventors: Martin M. Liphardt, Lincoln, NE (US); Christopher A. Goeden, Lincoln, NE (US)

(73) Assignee: J. A. Woollam Co., Inc., Lincoln, NE (US)

( * ) Notice: Subject to any disclaimer, the term of this patent is extended or adjusted under 35 U.S.C. 154(b) by 122 days.

(21) Appl. No.: 11/980,262

(22) Filed: Oct. 30, 2007

(65) Prior Publication Data

US 2008/0117413 A1 May 22, 2008

Related U.S. Application Data

(60) Continuation-in-part of application No. 11/495,130, filed on Jul. 29, 2006, now Pat. No. 7,333,198, and a division of application No. 11/177,207, filed on Jul. 8, 2005, now Pat. No. 7,084,978, and a continuation-in-part of application No. 11/145,470, filed on Jun. 6, 2005, now Pat. No. 7,327,456, and a continuation-in-part of application No. 10/943,821, filed on Sep. 17, 2004, now Pat. No. 7,295,313, and a continuation-in-part of application No. 10/652,696, filed on Sep. 2, 2003, now Pat. No. 7,230,699, and a continuation-in-part of application No. 10/376,677, filed on Feb. 28, 2003, now Pat. No. 6,982,792, and a continuation-in-part of application No. 10/178,723, filed on Jun. 24, 2002, now Pat. No. 6,950,182, and a continuation-in-part of application No. 09/864,840, filed on May 24, 2001, now Pat. No. 6,456,376, and a continuation-in-part of application No. 09/854,548, filed on May 14, 2001, now abandoned, and a continuation-in-part of application No. 09/583,229, filed on May 30, 2000, now Pat. No. 6,804,004, and a continuation-in-part of application No. 09/531,877, filed on Mar. 21, 2000, now Pat. No. 6,535,286.

(60) Provisional application No. 60/459,690, filed on Apr. 3, 2003, provisional application No. 60/588,315, filed on Jul. 15, 2004, provisional application No. 60/300,714, filed on Jun. 26, 2001, provisional application No. 60/424,589, filed on Nov. 7, 2002, provisional application No. 60/427,043, filed on Nov. 18, 2002, provisional application No. 60/431,489, filed on Dec. 6, 2002.

(51) Int. Cl.
*G01B 11/14* (2006.01)
(52) U.S. Cl. .................................................. 356/620
(58) Field of Classification Search ................ 356/375, 356/620, 369, 623, 399–401, 153
See application file for complete search history.

(56) References Cited

U.S. PATENT DOCUMENTS

| 4,373,817 A | 2/1983 | Coates | 356/636 |
| 5,045,704 A | 9/1991 | Coates | 250/372 |

(Continued)

OTHER PUBLICATIONS

PCT Publication WO 99/45340.

*Primary Examiner*—Tarifur R. Chowdhury
*Assistant Examiner*—Isiaka O Akanbi
(74) *Attorney, Agent, or Firm*—James D. Welch

(57) ABSTRACT

System and method for orienting the tilt and vertical position of samples in ellipsometer and the like systems.

19 Claims, 1 Drawing Sheet

U.S. PATENT DOCUMENTS

| | | | |
|---|---|---|---|
| RE34,783 E | 11/1994 | Coates | 250/372 |
| 5,412,473 A | 5/1995 | Rosencwaig et al. | 356/451 |
| 5,486,701 A | 1/1996 | Norton et al. | 250/372 |
| 5,596,411 A | 1/1997 | Fanton et al. | 356/369 |
| 5,608,526 A | 3/1997 | Piwonka-Corle | 356/369 |
| 5,798,837 A | 8/1998 | Aspnes et al. | 356/369 |
| 5,889,593 A | 3/1999 | Bareket et al. | 356/445 |
| 5,900,939 A | 5/1999 | Aspnes et al. | 356/369 |
| 5,910,842 A | 6/1999 | Piwonka-Corle | 356/369 |
| 6,091,499 A | 7/2000 | Abraham et al. | 356/375 |
| 6,600,560 B2 | 7/2003 | Mikkelsen et al. | 356/369 |
| 6,859,278 B1 * | 2/2005 | Johs et al. | 356/369 |
| 7,136,162 B1 * | 11/2006 | Liphardt et al. | 356/369 |
| 7,230,699 B1 * | 6/2007 | Liphardt et al. | 356/364 |
| 7,265,838 B1 * | 9/2007 | Johs et al. | 356/369 |
| 7,277,171 B1 * | 10/2007 | Johs et al. | 356/369 |
| 7,426,030 B1 * | 9/2008 | Liphardt et al. | 356/369 |
| 7,505,134 B1 * | 3/2009 | Johs et al. | 356/369 |
| 2002/0024668 A1 | 2/2002 | Stehle et al. | |
| 2008/0013089 A1 * | 1/2008 | Ishii et al. | 356/400 |

* cited by examiner

SAMPLE ORIENTATION SYSTEM AND METHOD

CROSS-REFERENCE TO RELATED APPLICATIONS

This application is a CIP of application Ser. No. 11/495,130 Filed Jul. 29, 2006 (now U.S. Pat. No. 7,333,198), and therevia this Application is a Divisional of patent application Ser. No. 11/177,207 Filed Jul. 8, 2005 (now U.S. Pat. No. 7,084,978), and therevia a CIP of 10/652,696 Filed Sep. 2, 2003 (now U.S. Pat. No. 7,230,699), and therevia Claims Benefit of Provisional Application Ser. No. 60/459,690 Filed Apr. 3, 2003. This Application also, via the foregoing Applications, Claims Benefit of Provisional Application Ser. No. 60/588,315 Filed Jul. 15, 2004. This application further is a CIP of application Ser. No. 11/145,470 Filed Jun. 6, 2005 (now U.S. Pat. No. 7,327,456), and therevia this application is a CIP of 10,376,677 Filed Feb. 28, 2003 (now U.S. Pat. No. 6,982,792), and therevia of Ser. Nos. 10/178,723 Filed Jun. 24, 2002, (now U.S. Pat. No. 6,950,182); 09/531,877 Filed Mar. 21, 2000 now U.S. Pat. No. 6,535,286; 09/583,229 Filed May 30, 2000, (now U.S. Pat. No. 6,804,004); 09/864,840 Filed May 24, 2001, (now U.S. Pat. No. 6,456,376); 10/943,821 Filed Sep. 17, 2004 now U.S. Pat. No. 7,295,313; 09/854,548 Filed May 14, 2001 now abandoned; and this application Claims benefit of Provisional Application Ser. Nos. 60/300,714 Filed Jun. 26, 2001; 60/424,589 Filed Nov. 7, 2002; 60/427,043 Filed Nov. 18, 2002; 60/431,489 Filed Dec. 6, 2002.

TECHNICAL FIELD

The disclosed invention relates to systems for adjusting sample orientation, and more particularly to system and method for orienting the tilt and vertical position of samples in ellipsometer and the like systems.

BACKGROUND

It is known to place samples on stages in ellipsometer and the like systems, and to cause a polarized beam of electromagnetic radiation to impinge on said sample at an oblique angle thereto, interact with said sample and then enter a detector. It is also known that the "tilt" of a sample surface at a specific location thereon can affect realized angle and plane of incidence values actually achieved. Further, it is known to adjust the vertical height of the stage to position a sample such that a beam of electromagnetic radiation reflecting therefrom enters a detector.

Existing Provisional and Utility Applications, (ie. 60/459,690 Filed Apr. 3, 2003 and Allowed application Ser. No. 10/652,696 Filed Sep. 2, 2003), by the Inventor herein, show a prior art system for detecting sample tilt, and a system which utilizes an ellipsometer beam reflected from a sample to perform vertical positioning of a stage. A beam splitter is used to divert a portion of the reflected beam into a detector and used to mediate adjustment of the sample's vertical position and/or tilt. Said system does not secure relative position of the ellipsometer and sample, but provides for aligning a sample system and controlling the angle and plane of incidence at which a beam of electromagnetic radiation obliquely impinges on a monitored location of a surface of a sample, and comprises, as viewed in side elevation:

a sample supporting stage which can be translated in "X", "Y" or "Z" directions as well as rotated about "X", "Y" and optionally "Z" axes;

vertically above said stage there being a first beam splitter means, a lens and a first camera means for providing a view of a portion of the surface of said sample, said first beam splitter means optionally having positioned on a lower surface thereof light emitting means for providing light to the surface of said sample;

laterally with respect to said first beam splitter means there being a reflection means;

vertically above said reflection means there being a second beam splitter;

vertically above said second beam splitter there being a second camera means and laterally with respect to said second beam splitter, there being sequentially a lens and an essentially point source of electromagnetic radiation;

said first and second camera means each having associated therewith display means.

Said system further comprises an ellipsometer polarization state generator to cause, and a polarization stage detector to monitor, a beam of electromagnetic radiation which in use impinges on said monitored location on said surface of said sample at an oblique angle thereto.

In use said first camera means and its associated display means provide a view of at least a portion of the surface of a sample utilizing light provided by said light emitting means for providing light to the surface of said sample positioned on said lower surface of said first beam splitter, and said essentially point source of electromagnetic radiation provides electromagnetic radiation to the surface of said sample via said second beam splitter, said reflective means and said first beam splitter, and said sample supporting stage is caused to be translated in any of said "X", "Y" and "Z" directions as well as rotated about said "X", "Y" and optionally "Z" axes which are necessary to cause an interrogating beam of electromagnetic radiation provided by said essentially point source of a source of electromagnetic radiation to reflect from the surface of said sample, proceed back through said first beam splitter means, reflect from said reflective means, pass through said second beam splitter means, enter said second camera means and cause an image on the display means associated therewith which indicates that the monitored location on the sample surface is oriented so as to face substantially vertically.

The purpose of the foregoing is to align said sample surface to assure that said beam of electromagnetic radiation provided to said monitored location on the surface of said sample at an oblique angle approaches said surface at known intended angle of incidence and plane of incidence orientation, rather than at an angle of incidence and plane of incidence orientation which is modified by surface irregularities or non-flat samples.

Said system can further comprise a polarizer means in the path of said beam of electromagnetic radiation provided by said essentially point source of electromagnetic radiation, and in which said first beam splitter is sensitive to polarization state, and the polarizer means can be adjustable to enable control of the direction of polarization. The system point source of a source of electromagnetic radiation can comprise a fiber optic.

A related Co-Pending Application is Ser. No. 11/495,130 Filed Jul. 29, 2006 which describes a related system.

A patent to Abraham et al., U.S. Pat. No. 6,091,499 describes a method and system for automatic relative adjustment of samples in relation to an ellipsometer. Paraphrasing, said Abraham et al. system basically comprises:

a system for orienting a sample on a stage in an ellipsometer system comprising a first light source, a polarizer, said stage, an analyzer and a detector;

said system further comprising a detection system having a second light source, wherein said detection system is independently adjustable in relation to said ellipsometer, and wherein said detection system can be electronically locked into position relative to said ellipsometer so that said ellipsometer and said detection system can be adjusted as one unit in relationship to said stage, wherein said detection system can detect both a tilt of a sample placed onto said stage, and a distance of said sample from a coordinate source of the ellipsometer in two perpendicular axes; and said system further comprising an adjusting device, wherein said adjusting device can adjust tilt of said stage, and wherein said adjusting device can adjust the position of said ellipsometer and detection system when in an electronically locked relationship with respect to one another.

The 499 patent drawings show a single source, (identified as (21)), provides, via beam splitters and reflection means, normal and oblique angle of incidence electromagnetic beams to a sample, which normal and oblique angle of incidence electromagnetic beams are each intercepted by a different detector, (identified as (24) and (25) respectively), after reflecting from the sample. The associated ellipsometer system comprises a separate source, (identified as (11)).

Additional known patents are:
Patent to Coates U.S. Pat. No. 4,373,817;
Patent to Coates U.S. Pat. No. 5,045,704;
RE. 34,783 to Coates;
Patent to Mikkelsen et al., U.S. Pat. No. 6,600,560;
Patent to Fanton et al., U.S. Pat. No. 5,596,411;
Patent to Piwonka-Corle et al., U.S. Pat. No. 5,910,842;
Patent to Piwonka-Corle et al., U.S. Pat. No. 5,608,526;
Patent to Bareket, U.S. Pat. No. 5,889,593;
Patent to Norton et al., U.S. Pat. No. 5,486,701;
Patent to Aspnes et al., U.S. Pat. No. 5,900,939;
Patent to Aspnes et al., U.S. Pat. No. 5,9798,837;
Patent to Rosenscwaig et al., U.S. Pat. No. 5,412,473;
Patent to Carter et al., U.S. Pat. No. 5,771,094;
Patent to Liphardt, U.S. Pat. No. 7,136,162;
PCT Application Publication WO 99/45340;
Published Application of Stehle et al., No. US2002/0024668 A1.

Need remains for additional systems and methods for orienting the vertical position, and tilt, of samples in ellipsometer, polarimeter, spectrophotometer and the like systems.

DISCLOSURE OF THE INVENTION

The present invention system for orienting a surface of a stage which optionally has a sample having a surface supported thereupon, can be described in "X"-"Y"-"Z" coordinate space, as comprising:

a) a stage for supporting a sample such that said surface of said stage or sample is oriented substantially in an "X"-"Y" plane and faces substantially in a "Z" axis direction;

b) a source of a beam of electromagnetic radiation oriented to direct a beam of electromagnetic radiation to impinge on said surface of said stage or sample placed upon said stage, at an oblique angle of incidence oriented substantially in a "Y"-"Z" plane;

c) a specular beam detector of a specularly reflected electromagnetic beam which results from said oblique angle of incidence beam specularly reflecting from said surface of said stage or sample in said substantially "Y"-"Z" plane;

d) a scattered beam detector comprising means for receiving scattered reflected electromagnetic radiation which results from said oblique angle of incidence beam non-specularly reflecting from said surface of said stage or sample;

e) first rotation effecting means for causing said stage to rotate substantially about at least one of said "X" and "Y" axis;

f) said stage and first rotation effecting means for causing said stage to rotate substantially about at least one of said "X" or "Y" axis being supported on translation means for moving said stage substantially in at least one of said "X" and "Y" directions;

g) said translation means for moving said stage substantially in said at least one of said "X" and "Y" direction being supported on a second rotation effecting means for causing said stage to rotate substantially about at least one of said "X" or "Y" axis; and h) said system further comprising means for changing the relative distance between:

said source of electromagnetic radiation oriented to cause a beam of electromagnetic radiation to impinge on a surface of said stage or a sample placed on said stage, at an oblique angle of incidence, and said stage;

along the substantially "Z" axis.

Said system can further comprise a combination source and detector for providing a beam of electromagnetic radiation and detecting a portion thereof which reflects from said stage or sample surface, said combination source and detector being positioned to direct a beam of electromagnetic radiation substantially along said "Z" axis such that it reflects from said surface of said stage or sample substantially back along said "Z" axis and is detected by said detector of the combination source and detector.

Said system can also further comprise at least one selection from the group consisting of:

a chopper or modulator in the beam path of said beam of electromagnetic radiation provided by said combination source and detector for providing a beam of electromagnetic radiation and detecting a portion thereof which reflects from said stage or sample surface substantially along said "Z" axis;

a chopper or modulator in the beam path of said beam of electromagnetic radiation provided by said source of electromagnetic radiation oriented to cause a beam of electromagnetic radiation to impinge on said surface of said stage or sample placed upon said stage, at an oblique angle of incidence in said substantially "Y"-"Z" plane;

a focusing means in the pathway of said beam of electromagnetic radiation caused to impinge on said surface of said stage or sample placed upon said stage, at an oblique angle of incidence, prior to said stage;

a focusing means in the pathway of said specular reflected beam of electromagnetic radiation which is caused to impinge on said surface of said stage or sample placed upon said stage, at an oblique angle of incidence, after said stage;

a polarization stage generator in the pathway of the beam provided by said source of electromagnetic radiation oriented to cause a beam of electromagnetic radiation to impinge on said surface of said stage or sample placed upon said stage, at an oblique angle of incidence oriented substantially in an "Y"-"Z" plane;

a polarization state analyzer in the pathway of the beam of electromagnetic beam provided by said source of electromagnetic radiation oriented to cause a beam of electromagnetic radiation to impinge on said surface of said stage or sample placed upon said stage, at an oblique angle of incidence oriented substantially in an "Y"-"Z" plane, which is specularly reflected from said stage or sample;

It is noted that translation in a substantially "X"-"Y" plane is effected by an r-0 approach.

A present invention method of orienting a surface of a stage which optionally has a sample supported thereupon, in "X"-"Y" "Z" coordinate space, comprises:

A) providing a system for orienting a surface of a stage which optionally has a sample supported thereupon, in "X"-"Y"-"Z" coordinate space as just described above;

B) causing said source of a beam of electromagnetic radiation oriented to provide a beam of electromagnetic radiation which impinges on said surface of said stage or sample placed upon said stage, at an oblique angle of incidence oriented substantially in a "Y"-"Z" plane, to provide a beam of electromagnetic radiation, along an oblique angle of incidence to the surface of said stage or sample placed thereupon;

C) while monitoring the output of said scattered beam detector which comprises means for receiving scattered reflected electromagnetic radiation which results from said oblique angle of incidence beam non-specularly reflected from said surface of said stage or sample, causing said translation means for moving said stage substantially in said at least one of said "X" and "Y" directions and if scattered beam detector output changes then causing said stage to rotate about said at least one axis and again causing said translation means for moving said stage substantially in said at least one of said "X" and "Y" directions to cause translation motion of said stage;

D) repeating step C if the output of said scattered beam detector changes when said translation means for moving said stage substantially in said at least one of said "X" and "Y" directions is caused to effect translation motion of said stage, and moving on to step E when said translation motion has substantially no effect on the output of said scattered beam detector;

E) while monitoring the output of said specular beam detector of a specularly reflected electromagnetic beam which results from said oblique angle of incidence beam specularly reflecting from said surface of said stage or sample in said substantially "Y"-"Z" plane, causing said second rotation effecting means for causing said stage to rotate substantially about at least one of said "X" and "Y" axis, to rotate about at least said substantially "X" axis so as to rotate said stage to a position which substantially maximizes the output of said specular beam detector.

Said method can involve providing a combination source and detector means for providing a beam of electromagnetic radiation and detecting a portion thereof which reflects from said stage or sample surface back thereto, said combination source and detector being positioned to direct an incident beam of electromagnetic radiation along a locus oriented substantially along said "Z" axis such that it reflects from the surface of said stage or sample; said method further comprises the step of:

F) saving and optionally calibrating the output of said detector of said combination source and detector means.

Said method can involve steps A-F being performed for the case wherein a sample was or was not present on said stage surface and wherein step F provided output of said detector of said combination source and detector means which defines an acceptable condition;

said method then can further comprise placing an investigation sample onto said stage surface and causing said source of electromagnetic radiation which is oriented to cause a beam of electromagnetic radiation to impinge on said surface of said stage or sample placed upon said stage at an oblique angle of incidence oriented substantially in an "Y"-"Z" plane, to cause a beam of electromagnetic radiation to impinge upon said investigation sample at a first location thereupon;

said method further comprising adjusting at least one selection from the group consisting of:
operating said first rotation effecting means for causing said stage to rotate substantially about at least one of said "X" and "Y" axis to cause rotation substantially about at least said "X" or "Y" axis; and
operating said system for changing the relative distance between:
said source of electromagnetic radiation oriented to cause a beam of electromagnetic radiation to impinge on a surface of said stage or a sample placed on said stage, at an oblique angle, and
said stage;
along the substantially "Z" axis;

until the output of said of said detector of the combination source and detector is substantially the same as that determined and saved and optionally calibrated in step F and/or the output of the specular beam detector is maximized.

Said method can also further comprise, in combination:
causing said translation means for moving said stage substantially in at least one of said "X" and "Y" directions to operate such that said beam of electromagnetic radiation impinges onto a location of said sample surface; and causing said means for changing the relative distance between:
said source of electromagnetic radiation oriented to cause a beam of electromagnetic radiation to impinge on a surface of said investigation sample placed on said stage, at an oblique angle, and
said stage;

along the substantially "Z" axis; to change the distance between said source of electromagnetic radiation oriented to cause a beam of electromagnetic radiation to impinge on a surface of said investigation sample placed on said stage at an oblique angle, so that the reflected beam of electromagnetic radiation caused to impinge on an investigation sample surface at an oblique angle, specularly continues to substantially maximally reflect into said specular beam detector.

Said method can further comprise providing a system which comprises a chopper or modulator in the beam path of said beam of electromagnetic radiation which is directed along a locus oriented substantially along said "Z" axis such that it reflects from the surface of said stage or sample oriented by steps A-F and is detected by said detector of said combination source and detector; and wherein said chopper or modulator is applied to alternatingly change intensity of said beam from a relatively high to a relatively low value.

It is to be understood that once the second rotation effecting means for causing said stage (STG) to rotate about at least said substantially "X" axis is operated, then an "X" translation of the stage will typically require changing the "Z" location of the sample in order to maintain the locus of the specularly reflected beam into the specular beam detector.

It is noted that the purpose of the second rotation effecting means is to allow orienting a sample, after it has been "flattened" by use of the first rotation effecting means in combination with the "X" and "Y" in steps C and D above, so that a normal to the surface of the test sample becomes oriented along the bisector of the angle between the locus of the incident and specularly reflected beams, such that the specularly reflected beam enters the specular beam detector.

As mentioned above, said method can involve effecting translation in the substantially "X"-"Y" plane is an r-θ approach.

Said method can further comprise providing a chopper or modulator in the beam path of said beam of electromagnetic radiation which is directed along a locus oriented substantially along said "Z" axis such that it reflects from the surface of said stage or sample oriented by the steps of and is detected by said detector of the combination source and detector; and applying said chopper or modulator to alternatingly change intensity of said beam from a relatively high to a relatively low value. This is beneficial in that the system can then be operated in a lighted room.

It should be noted that the foregoing description is very definite as regards a coordinate system to aid with describing the present invention system. As the coordinate system does not limit the invention, an alternative description is provided below. With that in mind, the present invention system for orienting a surface of a stage which optionally has a sample having a surface supported thereupon, can be described as comprising:

a) a stage for supporting a sample, wherein said surface of said stage or sample is oriented such that a normal thereto projects substantially along an arbitrary "N" axis;

b) a source of electromagnetic radiation oriented to cause a beam of electromagnetic radiation to impinge on said surface of said stage or sample placed upon said stage, at an oblique angle of incidence with respect to said arbitrary "N" axis;

c) a specular beam detector of a specularly reflected electromagnetic beam which results from said oblique angle of incidence beam specularly reflecting from said surface of said stage or sample;

d) a scattered beam detector comprising means for receiving scattered reflected electromagnetic radiation which results from said oblique angle of incidence beam non-specularly reflecting from said surface of said stage or sample;

e) first rotation effecting means for causing said stage to rotate about axes which are substantially perpendicular to said arbitrary "N" axis;

f) said stage and first rotation effecting means for causing said stage to rotate being supported on translation means for moving said stage in a plane which is substantially perpendicular to said arbitrary "N" axis;

g) said translation means being supported on a second rotation effecting means for causing said stage to rotate about axes which are substantially perpendicular to said arbitrary "N" axis; and h) said system further comprising means for changing the relative distance between:

said source of electromagnetic radiation oriented to cause a beam of electromagnetic radiation to impinge on a surface of a said stage or sample placed on said stage, at an oblique angle of incidence with respect to said arbitrary "N" axis direction, and said stage;

substantially along the arbitrary "N" axis.

Said system can further comprise a combination source and detector for providing a beam of electromagnetic radiation and detecting a portion thereof which reflects from said stage or sample surface, said combination source and detector being positioned to direct a beam of electromagnetic radiation substantially along said arbitrary "N" axis such that it reflects from the surface of said stage or sample substantially back along said arbitrary "N" axis and is detected by said detector of the combination source and detector.

Said system can also further comprises at least one selection from the group consisting of:

a chopper or modulator in the beam path of said beam of electromagnetic radiation provided by said combination source and detector for providing a beam of electromagnetic radiation and detecting a portion thereof which reflects from said stage or sample surface, substantially along said arbitrary "N" axis;

a chopper or modulator in the beam path of said beam of electromagnetic radiation provided by said source of electromagnetic radiation oriented to cause a beam of electromagnetic radiation to impinge on said surface of said stage or sample placed upon said stage, at an oblique angle of incidence with respect to said arbitrary "N" axis;

a focusing means in the pathway of said beam of electromagnetic radiation caused to impinge on said surface of said stage or sample placed upon said stage, at an oblique angle of incidence with respect to said arbitrary "N" axis, prior to said stage;

a focusing means in the pathway of said specular reflected beam of electromagnetic radiation which is caused to impinge on said surface of said stage or sample placed upon said stage, at an oblique angle of incidence with respect to said arbitrary "N" axis, after said stage;

a polarization stage generator in the pathway of the beam provided by said source of electromagnetic radiation oriented to cause a beam of electromagnetic radiation to impinge on said surface of said stage or sample placed upon said stage, at an oblique angle of incidence with respect to said arbitrary "N" axis;

a polarization state analyzer in the pathway of the beam of electromagnetic beam provided by said source of electromagnetic radiation oriented to cause a beam of electromagnetic radiation to impinge on said surface of said stage or sample placed upon said stage at an oblique angle of incidence with respect to said arbitrary "N" axis, and is specularly reflected from said stage or sample surface;

A present invention method of orienting a surface of a stage which optionally has a sample supported thereupon can comprise:

A) providing a system for orienting a surface of a stage which optionally has a sample having a surface supported thereupon as described just above:

B) causing said source of a beam of electromagnetic radiation oriented to cause a beam of electromagnetic radiation to impinge on said surface of said stage or sample placed upon said stage, at an oblique angle of incidence to provide a beam of electromagnetic radiation, along an oblique angle of incidence to the surface of said stage or sample placed thereupon;

C) while monitoring the output of said scattered beam detector which comprises means for receiving scattered reflected electromagnetic radiation which results from said oblique angle of incidence beam non-specularly reflected from said surface of said stage or sample, causing said translation means for moving said stage in a plane which is substantially perpendicular to said arbitrary "N" axis to cause translation motion of said stage and if said scattered beam detector output changes than then causing said first rotation means to cause rotation of said stage about said at least one of said axes which is substantially perpendicular to said arbitrary "N" axis and again causing said translation means for moving said stage in a plane which is substantially perpendicular to said arbitrary "N" axis to cause translation motion of said stage;

D) repeating step C if the output of said scattered beam detector changes when said translation means for moving said stage in a plane which is substantially perpendicular to said arbitrary "N" axis causes is caused to effect translation motion of said stage and moving on to step E when said translation motion has substantially no effect on the output of said scattered beam detector;

E) while monitoring the output of said specular beam detector of a specularly reflected electromagnetic beam which results from said oblique angle of incidence beam specularly reflecting from said surface of said stage or sample causing said second rotation effecting means for causing said stage to rotate substantially about at least one of said axes which is substantially perpendicular to said arbitrary "N" axis to a position which substantially maximizes the output of said specular beam detector.

Said method can involve providing a system which further comprises a combination source and detector means for providing a beam of electromagnetic radiation and detecting a portion thereof which reflects from said stage or sample surface back thereto, said combination source and detector being positioned to direct an incident beam of electromagnetic radiation along a locus oriented substantially along said arbitrary "N" axis such that it reflects from the surface of said stage or sample;

said method further comprises the step of:

F) saving and optionally calibrating the output of said detector of said combination source and detector means.

Said method, in which the steps A-F were performed for the case wherein a sample was or was not present on said stage surface and wherein step F provided output of said detector of said combination source and detector means which defines an acceptable condition;

can further comprise placing an investigation sample onto said stage surface and causing said source of electromagnetic radiation which is oriented to cause a beam of electromagnetic radiation to impinge on said surface of said stage or sample placed upon said stage at an oblique angle of incidence oriented, to cause a beam of electromagnetic radiation to impinge upon said investigation sample at a location thereupon;

said method further comprising adjusting at least one selection from the group consisting of:
  operating said first rotation effecting means for causing said stage to rotate about axes which are substantially perpendicular to said arbitrary "N" axis; and
  operating said system for changing the relative distance between:
    said source of electromagnetic radiation oriented to cause a beam of electromagnetic radiation to impinge on a surface of a said stage or a sample placed on said stage, at an oblique angle, and
    said stage;
  along said arbitrary "N" axis;

until the output of said of said detector of the combination source and detector is substantially the same as that determined and saved and optionally calibrated in step F and/or the output of the specular beam detector is maximized.

Said method can further comprise, in the step of providing a system for orienting a surface of a stage which optionally has a sample having a surface supported thereupon, providing at least one selection from the group consisting of:

a chopper or modulator in the beam path of said beam of electromagnetic radiation provided by said combination source and detector for providing a beam of electromagnetic radiation and detecting a portion thereof which reflects from said stage or sample surface, substantially along said arbitrary "N" axis;

a chopper or modulator in the beam path of said beam of electromagnetic radiation provided by said source of electromagnetic radiation oriented to cause a beam of electromagnetic radiation to impinge on said surface of said stage or sample placed upon said stage, at an oblique angle of incidence with respect to said arbitrary "N" axis;

a focusing means in the pathway of said beam of electromagnetic radiation caused to impinge on said surface of said stage or sample placed upon said stage, at an oblique angle of incidence with respect to said arbitrary "N" axis, prior to said stage;

a focusing means in the pathway of said specular reflected beam of electromagnetic radiation which is caused to impinge on said surface of said stage or sample placed upon said stage, at an oblique angle of incidence with respect to said arbitrary "N" axis, after said stage;

a polarization stage generator in the pathway of the beam provided by said source of electromagnetic radiation oriented to cause a beam of electromagnetic radiation to impinge on said surface of said stage or sample placed upon said stage, at an oblique angle of incidence with respect to said arbitrary "N" axis;

a polarization state analyzer in the pathway of the beam of electromagnetic beam provided by said source of electromagnetic radiation oriented to cause a beam of electromagnetic radiation to impinge on said surface of said stage or sample placed upon said stage at an oblique angle of incidence with respect to said arbitrary "N" axis, and is specularly reflected from said stage or sample surface;

It is noted that in Step C of the above recited methodology, the detector which indicates scattered beam detector output change is typically a CCD Camera, and the output is change in location or focus of a spot identified thereby. It is also noted that the scattered beam detector can be replaced with other height detection means, such as a profilometer, or a quad detector placed in the reflected specular beam. In the later case, it is noted, the optional focusing lens (F1) must be present.

It is also noted that in Step F of the above recited methodology, the output of the detector of the combination source and detector means which is desired can be stored directly as the goal which indicates proper alignment, or the readout of said detector can be "calibrated" to read, for instance, "X"="0" & "Y"="0", in an "X"-"Y" coordinate system. The later approach can make it easier to perform alignment for different samples.

The present invention methodology can include performing at least one selection from the group consisting of:
  storing at least some data provided by a detector in machine readable media;
  analyzing at least some of the data provided by a detector and storing at least some of the results of said analysis in machine readable media;
  displaying at least some data provided by a detector by electronic and/or non-electronic means;
  analyzing at least some of the data provided by a detector and displaying at least some of the results of said analysis by electronic and/or non-electronic means;

causing at least some data provided by a detector to produce a signal which is applied to provide a concrete and tangible result;

analyzing at least some of the data provided by a detector and causing at least some thereof to produce a signal which is applied to provide a concrete and tangible result.

Further, it is noted that the present invention methodology causes a change in orientation of a stage and/or sample, and causes change in polarization state of an oblique angle of incidence of a beam of electromagnetic radiation by interacting with a sample. These are examples of concrete and tangible changes.

The present invention will be better understood by reference to the Detailed Description Section of this Specification, in conjunction with the Drawings.

DETAILED DESCRIPTION

Figure 1:
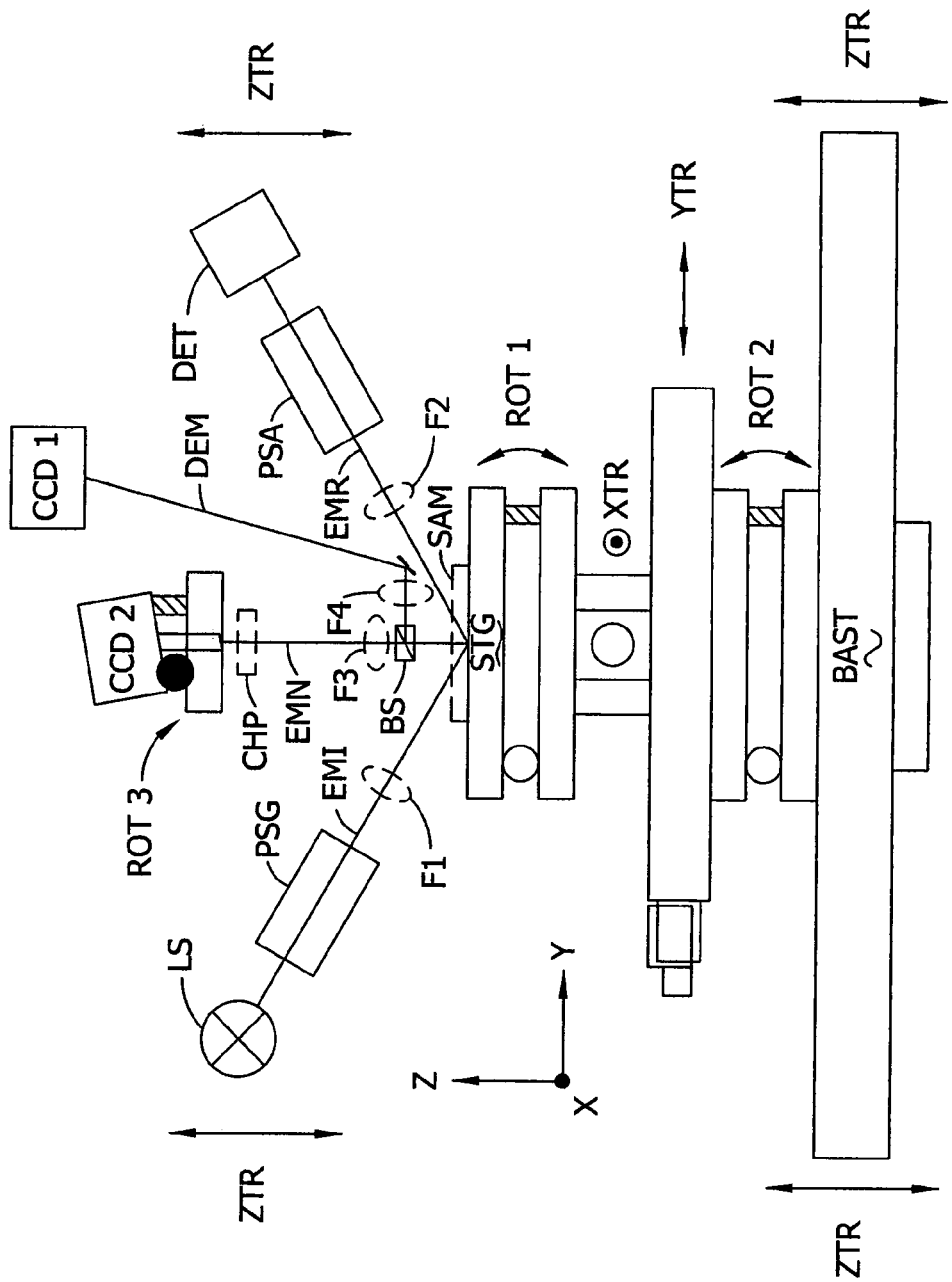
FIG. 1 shows the system of the present invention.

Turning now to FIG. 1, a system of the present invention for orienting a surface of a stage which optionally has a sample supported thereupon, can be seen in "X"-"Y"-"Z" coordinate space, to comprise:

a) a stage (STG) for supporting a sample (SAM) such that said surface of said stage (STG) or sample (SAM) is oriented substantially in an "X"-"Y" plane and faces substantially in a "Z" axis direction;

b) a source (LS) of electromagnetic radiation oriented to cause a beam of electromagnetic radiation (EMI) to impinge on said surface of said stage (STG) or sample (SAM) placed upon said stage (STG), at an oblique angle of incidence oriented substantially in an "Y"-"Z" plane;

c) a specular beam detector (DET) of a specularly reflected electromagnetic beam which results from said oblique angle of incidence beam specularly reflecting from said surface of said stage (STG) or sample (SAM) in said substantially "Y"-"Z" plane;

d) a scattered beam detector (CCD1) comprising means for receiving scattered reflected electromagnetic radiation which results from said oblique angle of incidence beam non-specularly reflecting from said surface of said stage (STG) or sample (SAM);

e) first rotation effecting means (ROT1) for causing said stage (STG) to rotate about "X" and/or "Y" axes;

f) said stage (STG) and first rotation effecting means (ROT1) for causing said stage (STG) to rotate about "X" and/or "Y" axes being supported on "X"-"Y" axis translation means ((XTR) & (YTR)) for moving said stage (STG) in the substantial "X"-"Y" plane of said surface of said stage (STG) or sample (SAM) resting thereupon, (co-ordinated operation of said (ROT1) and (XTR) and (YTR) enabling achieving "flattening" of a sample such that "X" and "Y translation has no effect on the direction of a specularly reflected beam therefrom);

g) said "X"-"Y" axis translation means ((XTR) & (YTR)) being supported on a second rotation effecting means (ROT2) for causing said stage (STG) to rotate about at least said substantially "X" axis, (said (ROT2) allowing orienting a normal to the sample surface along a bisector of the angle between incident (EMI) and specularly reflected (EMO) beams); and h) said system further comprising means for changing the relative distance (ZTR) between:

said source (LS) of electromagnetic radiation oriented to cause a beam of electromagnetic radiation to impinge on a surface of said stage (STG) or a sample (SAM) placed on said stage (STG), at an oblique angle of incidence, and said stage (STG);

along the substantially "Z" axis. Said means for changing the relative distance (ZTR) is shown only functionally and it is to be appreciated that change in location along the "Z" axis can be achieved by motion of either the basic stage (BAST) or by movement of the source (LS) and/or detector (DET) of the electromagnetic radiation (EMI) (EMO) which proceeds along the oblique angle of incidence locus. It is to be understood that said means for changing the relative distance (ZTR) is necessary as once the second rotation effecting means (ROT2) for causing said stage (STG) to rotate about at least said substantially "X" axis is operated to properly orient the normal to the sample (SAM) surface along the bisector of the angle between the incident (EMI) and specularly reflected (EMO) beams, then an "X" translation of the stage (STG) will typically necessitate changing the "Z" location of the sample (SAM) in order to maintain the locus of the specularly reflected beam (EMO) into the specular beam detector (DET).

It is also to be noted that the electromagnetic radiation (EMI) can be polarized by a polarization state generator (PSG) and analyzed by a polarization state analyzer (PSA), in which case the Source (LS), polarization state generator (PSG), polarization state analyzer (PSA) and detector (DET) are components of an ellipsometer or polarimeter. It is additionally noted that focusing means (F1) and collimating means (F2) can be utilized to cause a small spot image on the stage (STG) or sample (SAM). Further, note that a beam splitter (BS) followed by a focusing means (F4) can be included, with diverted electromagnetic radiation (DEM) directed to said a scattered beam detector (CCD1).

FIG. 1 also shows a combination source and detector (CCD2) for providing a beam of electromagnetic radiation (EMN) and detecting a portion thereof which reflects from said stage (STG) or sample (SAM) surface, said combination source and detector (CCD2) being positioned to direct a beam of electromagnetic radiation substantially along said "Z" axis such that it reflects from the surface of said stage (STG) or sample (SAM) substantially back along said "Z" axis and is detected by said detector of the combination source and detector. Note also that said system can further comprises a chopper or modulator (CHP) in the beam path of said beam of electromagnetic radiation. Further shown is a third rotation means (ROT3) positioned to allow the combination source and detector (CCD2) to be rotated about at least one axis. This can be used make said detector in the combination source and detector (CCD2) to read a convenient value when the stage (STG) is properly oriented. Also, the present invention system can include a focusing means (F3) in the beam (EMN) path.

FIG. 1 also shows that the present invention system can further comprise a chopper or modulator and/or a focusing means in the beam of path said beam of electromagnetic radiation provided by said combination source and detector for providing a beam of electromagnetic radiation and detecting a portion thereof which reflects from said stage or sample surface, said combination source and detector being positioned to direct a beam of electromagnetic radiation substantially along said "Z" axis such that it reflects from the surface of said stage or sample substantially back along said "Z" axis and is detected by said detector of the combination source and detector. The major purpose of including a chopper or modulator is to enable use in a lighted room.

FIG. 1 also shows that the present invention system can further comprise a focusing means in the pathway of said beam of electromagnetic radiation caused to impinge on said surface of said stage or sample placed upon said stage, at an oblique angle of incidence, prior to said stage.

FIG. 1 also shows that the present invention system can further comprise a focusing means, (ie. collimating), in the pathway of said specular reflected beam of electromagnetic radiation which is caused to impinge on said surface of said stage or sample placed upon said stage, at an oblique angle of incidence, after said stage.

It is generally to be understood that while "X"-"Y" plane motion is described, said translation can be achieved by an r-θ approach wherein said stage (STG) is rotated and the radius from a center point changed.

While "X"-"Y"-"Z" coordinates were used in the foregoing for clarity and ease of disclosure, it is to be understood that it is not necessary to orient the present invention system in any absolute sense for the system to be within the scope of the Claims. For instance, as found in the Disclosure of the Invention Section of this Specification, the present invention system can be described by referencing everything to a normal (N) to the surface of the Stage (STG) or a Sample (SAM) thereupon.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A system for orienting a surface of a stage which optionally has a sample having a surface supported thereupon, in "X"-"Y"-"Z" coordinate space, comprising:
   a) a stage for supporting a sample such that said surface of said stage or sample is oriented substantially in an "X"-"Y" plane and faces substantially in a "Z" axis direction;
   b) a source of a beam of electromagnetic radiation oriented to direct a beam of electromagnetic radiation to impinge on said surface of said stage or sample placed upon said stage, at an oblique angle of incidence oriented substantially in a "Y"-"Z" plane;
   c) a specular beam detector of a specularly reflected electromagnetic beam which results from said oblique angle of incidence beam specularly reflecting from said surface of said stage or sample in said substantially "Y"-"Z" plane;
   d) a scattered beam detector comprising means for receiving scattered reflected electromagnetic radiation which results from said oblique angle of incidence beam non-specularly reflecting from said surface of said stage or sample;
   e) first rotation effecting means for causing said stage to rotate substantially about at least one of said "X" and "Y" axis;
   f) said stage and first rotation effecting means for causing said stage to rotate substantially about at least one of said "X" or "Y" axis being supported on translation means for moving said stage substantially in at least one of said "X" and "Y" directions;
   g) said translation means for moving said stage substantially in said at least one of said "X" and "Y" direction being supported on a second rotation effecting means for causing said stage to rotate substantially about at least one of said "X" or "Y" axis; and
   h) said system further comprising means for changing the relative distance between:
      said source of electromagnetic radiation oriented to cause a beam of electromagnetic radiation to impinge on a surface of said stage or a sample placed on said stage, at an oblique angle of incidence, and
      said stage;
   along the substantially "Z" axis.

2. A system as in claim 1, which further comprises a combination source and detector for providing a beam of electromagnetic radiation and detecting a portion thereof which reflects from said stage or sample surface, said combination source and detector being positioned to direct a beam of electromagnetic radiation substantially along said "Z" axis such that it reflects from said surface of said stage or sample substantially back along said "Z" axis and is detected by said detector of the combination source and detector.

3. A system as in claim 2, which further comprises at least one selection from the group consisting of:
   a chopper or modulator in the beam path of said beam of electromagnetic radiation provided by said combination source and detector for providing a beam of electromagnetic radiation and detecting a portion thereof which reflects from said stage or sample surface substantially along said "Z" axis;
   a chopper or modulator in the beam path of said beam of electromagnetic radiation provided by said source of electromagnetic radiation oriented to cause a beam of electromagnetic radiation to impinge on said surface of said stage or sample placed upon said stage, at an oblique angle of incidence in said substantially "Y"-"z" plane;
   a focusing means in the pathway of said beam of electromagnetic radiation caused to impinge on said surface of said stage or sample placed upon said stage, at an oblique angle of incidence, prior to said stage;
   a focusing means in the pathway of said specular reflected beam of electromagnetic radiation which is caused to impinge on said surface of said stage or sample placed upon said stage, at an oblique angle of incidence, after said stage;
   a polarization stage generator in the pathway of the beam provided by said source of electromagnetic radiation oriented to cause a beam of electromagnetic radiation to impinge on said surface of said stage or sample placed upon said stage, at an oblique angle of incidence oriented substantially in an "Y"-"Z" plane;
   a polarization state analyzer in the pathway of the beam of electromagnetic beam provided by said source of electromagnetic radiation oriented to cause a beam of electromagnetic radiation to impinge on said surface of said stage or sample placed upon said stage, at an oblique angle of incidence oriented substantially in an "Y"-"Z" plane, which is specularly reflected from said stage or sample.

4. A system as in claim 1 in which translation in the substantially "X"-"Y" plane is effected by an r-θ approach.

5. A method of orienting a surface of a stage which optionally has a sample supported thereupon, in "X"-"Y"-"Z" coordinate space, comprising:
   A) providing a system for orienting a surface of a stage which optionally has a sample supported thereupon, in "X"-"Y"-"Z" coordinate space, which comprises:

a) a stage for supporting a sample such that said surface of said stage or sample is oriented substantially in an "X"-"Y" plane and faces substantially in a "Z" axis direction;

b) a source of a beam of electromagnetic radiation oriented to direct a beam of electromagnetic radiation to impinge on said surface of said stage or sample placed upon said stage, at an oblique angle of incidence oriented substantially in a "Y"-"Z" plane;

c) a specular beam detector of a specularly reflected electromagnetic beam which results from said oblique angle of incidence beam specularly reflecting from said surface of said stage or sample in said substantially "Y"-"Z" plane;

d) a scattered beam detector comprising means for receiving scattered reflected electromagnetic radiation which results from said oblique angle of incidence beam non-specularly reflecting from said surface of said stage or sample;

e) first rotation effecting means for causing said stage to rotate substantially about at least one of said "X" and "Y" axis;

f) said stage and first rotation effecting means for causing said stage to rotate substantially about at least one of said "X" or "Y" axis being supported on translation means for moving said stage substantially in at least one of said "X" and "Y" directions;

g) said translation means for moving said stage substantially in said at least one of said "X" and "Y" direction being supported on a second rotation effecting means for causing said stage to rotate substantially about at least one of said "X" or "Y" axis; and h) said system further comprising means for changing the relative distance between:
said source of electromagnetic radiation oriented to cause a beam of electromagnetic radiation to impinge on a surface of said stage or a sample placed on said stage, at an oblique angle of incidence, and
said stage;
along the substantially "Z" axis;

B) causing said source of a beam of electromagnetic radiation oriented to provide a beam of electromagnetic radiation which impinges on said surface of said stage or sample placed upon said stage, at an oblique angle of incidence oriented substantially in a "Y"-"Z" plane, to provide a beam of electromagnetic radiation, along an oblique angle of incidence to the surface of said stage or sample placed thereupon;

C) while monitoring the output of said scattered beam detector which comprises means for receiving scattered reflected electromagnetic radiation which results from said oblique angle of incidence beam non-specularly reflected from said surface of said stage or sample, causing said translation means for moving said stage substantially in said at least one of said "X" and "Y" directions to move said stage in at least one of the "X" and "Y" directions, and if scattered beam detector output changes then causing said stage to rotate about said at least one axis and again causing said translation means for moving said stage substantially in at least one of said "X" and "Y" directions to cause translation motion of said stage;

D) repeating step C if the output of said scattered beam detector changes when said translation means for moving said stage substantially in said at least one of said "X" and "Y" directions is caused to effect translation motion of said stage, and moving on to step E when said translation motion has substantially no effect on the output of said scattered beam detector;

E) while monitoring the output of said specular beam detector of a specularly reflected electromagnetic beam which results from said oblique angle of incidence beam specularly reflecting from said surface of said stage or sample in said substantially "y"-"z" plane, causing said second rotation effecting means for causing said stage to rotate substantially about at least one of said "X" and "Y" axis, to rotate about at least said substantially "X" axis so as to rotate said stage to a position which substantially maximizes the output of said specular beam detector;

said change in orientation or position of said stage or sample constituting a concrete and tangible change.

6. A method as in claim 5 in which said system further comprises a combination source and detector means for providing a beam of electromagnetic radiation and detecting a portion thereof which reflects from said stage or sample surface back thereto, said combination source and detector being positioned to direct an incident beam of electromagnetic radiation along a locus oriented substantially along said "Z" axis such that it reflects from the surface of said stage or sample;

said method further comprises the step of:

F) saving and optionally calibrating the output of said detector of said combination source and detector means.

7. A method as in claim 6 in which the steps A-F were performed for the case wherein a sample was or was not present on said stage surface and wherein step F provided output of said detector of said combination source and detector means which defines an acceptable condition;

said method further comprising placing an investigation sample onto said stage surface and causing said source of electromagnetic radiation which is oriented to cause a beam of electromagnetic radiation to impinge on said surface of said stage or sample placed upon said stage at an oblique angle of incidence oriented substantially in an "Y"-"Z" plane, to cause a beam of electromagnetic radiation to impinge upon said investigation sample at a first location thereupon;

said method further comprising adjusting at least one selection from the group consisting of:
operating said first rotation effecting means for causing said stage to rotate substantially about at least one of said "X" and "Y" axis to cause rotation substantially about at least said "X" or "Y" axis; and
operating said system for changing the relative distance between:
said source of electromagnetic radiation oriented to cause a beam of electromagnetic radiation to impinge on a surface of said stage or a sample placed on said stage, at an oblique angle, and
said stage;
along the substantially "Z" axis;
until the output of said of said detector of the combination source and detector is substantially the same as that determined and saved and optionally calibrated in step F and/or the output of the specular beam detector is maximized.

8. A method as in claim 7 which further comprises, in combination:
causing said translation means for moving said stage substantially in at least one of said "X" and "Y" directions to operate such that said beam of electromagnetic radiation impinges onto a location of said sample surface; and causing said means for changing the relative distance between:
  said source of electromagnetic radiation oriented to cause a beam of electromagnetic radiation to impinge on a surface of said investigation sample placed on said stage, at an oblique angle, and
  said stage;
along the substantially "z" axis; to change the distance between said source of electromagnetic radiation oriented to cause a beam of electromagnetic radiation to impinge on a surface of a said investigation sample placed on said stage at an oblique angle, so that the reflected beam of electromagnetic radiation caused to impinge on a investigation sample surface at an oblique angle, specularly continues to substantially maximally reflect into said specular beam detector.

9. A method as in claim 6, wherein said system further comprises a chopper or modulator in the beam path of said beam of electromagnetic radiation which is directed along a locus oriented substantially along said "Z" axis such that it reflects from the surface of said stage or sample oriented by steps A-F and is detected by said detector of said combination source and detector; and wherein said chopper or modulator is applied to alternatingly change intensity of said beam from a relatively high to a relatively low value.

10. A method as in claim 5 wherein translation in the substantially "x"-"y" plane is effected by an r-θ motion approach.

11. A system for orienting a surface of a stage which optionally has a sample having a surface supported thereupon, comprising:
  a) a stage for supporting a sample, wherein said surface of said stage or sample is oriented such that a normal thereto projects substantially along an arbitrary "N" axis;
  b) a source of electromagnetic radiation oriented to cause a beam of electromagnetic radiation to impinge on said surface of said stage or sample placed upon said stage, at an oblique angle of incidence with respect to said arbitrary "N" axis;
  c) a specular beam detector of a specularly reflected electromagnetic beam which results from said oblique angle of incidence beam specularly reflecting from said surface of said stage or sample;
  d) a scattered beam detector comprising means for receiving scattered reflected electromagnetic radiation which results from said oblique angle of incidence beam non-specularly reflecting from said surface of said stage or sample;
  e) first rotation effecting means for causing said stage to rotate about axes which are substantially perpendicular to said arbitrary "N" axis;
  f) said stage and first rotation effecting means for causing said stage to rotate being supported on translation means for moving said stage in a plane which is substantially perpendicular to said arbitrary "N" axis;
  g) said translation means being supported on a second rotation effecting means for causing said stage to rotate about axes which are substantially perpendicular to said arbitrary "N" axis; and
  h) said system further comprising means for changing the relative distance between:
    said source of electromagnetic radiation oriented to cause a beam of electromagnetic radiation to impinge on a surface of said stage or a sample placed on said stage, at an oblique angle of incidence with respect to said arbitrary "N" axis direction, and
    said stage;
  substantially along the arbitrary "N" axis.

12. A system as in claim 11, which further comprises a combination source and detector for providing a beam of electromagnetic radiation and detecting a portion thereof which reflects from said stage or sample surface, said combination source and detector being positioned to direct a beam of electromagnetic radiation substantially along said arbitrary "N" axis such that it reflects from the surface of said stage or sample substantially back along said arbitrary "N" axis and is detected by said detector of the combination source and detector.

13. A system as in claim 12, which further comprises at least one selection from the group consisting of:
  a chopper or modulator in the beam path of said beam of electromagnetic radiation provided by said combination source and detector for providing a beam of electromagnetic radiation and detecting a portion thereof which reflects from said stage or sample surface, substantially along said arbitrary "N" axis;
  a chopper or modulator in the beam path of said beam of electromagnetic radiation provided by said source of electromagnetic radiation oriented to cause a beam of electromagnetic radiation to impinge on said surface of said stage or sample placed upon said stage, at an oblique angle of incidence with respect to said arbitrary "N" axis;
  a focusing means in the pathway of said beam of electromagnetic radiation caused to impinge on said surface of said stage or sample placed upon said stage, at an oblique angle of incidence with respect to said arbitrary "N" axis, prior to said stage;
  a focusing means in the pathway of said specular reflected beam of electromagnetic radiation which is caused to impinge on said surface of said stage or sample placed upon said stage, at an oblique angle of incidence with respect to said arbitrary "N" axis, after said stage;
  a polarization stage generator in the pathway of the beam provided by said source of electromagnetic radiation oriented to cause a beam of electromagnetic radiation to impinge on said surface of said stage or sample placed upon said stage, at an oblique angle of incidence with respect to said arbitrary "N" axis;
  a polarization state analyzer in the pathway of the beam of electromagnetic beam provided by said source of electromagnetic radiation oriented to cause a beam of electromagnetic radiation to impinge on said surface of said stage or sample placed upon said stage at an oblique angle of incidence with respect to said arbitrary "N" axis, and is specularly reflected from said stage or sample surface.

14. A method of orienting a surface of a stage which optionally has a sample supported thereupon, comprising:
  A) providing a system for orienting a surface of a stage which optionally has a sample having a surface supported thereupon, comprising:
    a) a stage for supporting a sample, wherein said surface of said stage or sample is oriented such that a normal thereto projects substantially along an arbitrary "N" axis;
    b) a source of electromagnetic radiation oriented to cause a beam of electromagnetic radiation to impinge on said surface of said stage or sample placed upon said stage, at an oblique angle of incidence with respect to said arbitrary "N" axis;
    c) a specular beam detector of a specularly reflected electromagnetic beam which results from said oblique angle of incidence beam specularly reflecting from said surface of said stage or sample;

d) a scattered beam detector comprising means for receiving scattered reflected electromagnetic radiation which results from said oblique angle of incidence beam non-specularly reflecting from said surface of said stage or sample;

e) first rotation effecting means for causing said stage to rotate about axes which are substantially perpendicular to said arbitrary "N" axis;

f) said stage and first rotation effecting means for causing said stage to rotate being supported on translation means for moving said stage in a plane which is substantially perpendicular to said arbitrary "N" axis;

g) said translation means being supported on a second rotation effecting means for causing said stage to rotate about axes which are substantially perpendicular to said arbitrary "N" axis; and h) said system further comprising means for changing the relative distance between:
   said source of electromagnetic radiation oriented to cause a beam of electromagnetic radiation to impinge on a surface of said stage or a sample placed on said stage, at an oblique angle of incidence with respect to said arbitrary "N" axis direction, and
   said stage;
substantially along the arbitrary "N" axis;

B) causing said source of a beam of electromagnetic radiation oriented to cause a beam of electromagnetic radiation to impinge on said surface of said stage or sample placed upon said stage, at an oblique angle of incidence to provide a beam of electromagnetic radiation, along an oblique angle of incidence to the surface of said stage or sample placed thereupon;

C) while monitoring the output of said scattered beam detector which comprises means for receiving scattered reflected electromagnetic radiation which results from said oblique angle of incidence beam non-specularly reflected from said surface of said stage or sample, causing said translation means for moving said stage in a plane which is substantially perpendicular to said arbitrary "N" axis to cause translation motion of said stage and if said scattered beam detector output changes than then causing said first rotation means to cause rotation of said stage about said at least one of said axes which is substantially perpendicular to said arbitrary "N" axis and again causing said translation means for moving said stage in a plane which is substantially perpendicular to said arbitrary "N" axis to cause translation motion of said stage;

D) repeating step C if the output of said scattered beam detector changes when said translation means for moving said stage in a plane which is substantially perpendicular to said arbitrary "N" axis causes is caused to effect translation motion of said stage and moving on to step E when said translation motion has substantially no effect on the output of said scattered beam detector;

E) while monitoring the output of said specular beam detector of a specularly reflected electromagnetic beam which results from said oblique angle of incidence beam specularly reflecting from said surface of said stage or sample causing said second rotation effecting means for causing said stage to rotate substantially about at least one of said axes which is substantially perpendicular to said arbitrary "N" axis to a position which substantially maximizes the output of said specular beam detector;

said change in orientation or position of said stage or sample constituting a concrete and tangible change.

15. A method as in claim 14 in which said system further comprises a combination source and detector means for providing a beam of electromagnetic radiation and detecting a portion thereof which reflects from said stage or sample surface back thereto, said combination source and detector being positioned to direct an incident beam of electromagnetic radiation along a locus oriented substantially along said arbitrary "N" axis such that it reflects from the surface of said stage or sample;
   said method further comprises the step of:
      F) saving and optionally calibrating the output of said detector of said combination source and detector means.

16. A method as in claim 15 in which the steps A-F were performed for the case wherein a sample was or was not present on said stage surface and wherein step F provided output of said detector of said combination source and detector means which defines an acceptable condition;
   said method further comprising placing an investigation sample onto said stage surface and causing said source of electromagnetic radiation which is oriented to cause a beam of electromagnetic radiation to impinge on said surface of said stage or sample placed upon said stage at an oblique angle of incidence oriented, to cause a beam of electromagnetic radiation to impinge upon said investigation sample at a location thereupon;
   said method further comprising adjusting at least one selection from the group consisting of:
      operating said first rotation effecting means for causing said stage to rotate about axes which are substantially perpendicular to said arbitrary "N" axis; and
      operating said system for changing the relative distance between:
         said source of electromagnetic radiation oriented to cause a beam of electromagnetic radiation to impinge on a surface of a said stage or a sample placed on said stage, at an oblique angle, and
         said stage;
      along said arbitrary "N" axis;
   until the output of said of said detector of the combination source and detector is substantially the same as that determined and saved and optionally calibrated in step F and/or the output of the specular beam detector is maximized.

17. A method as in claim 14, which further comprises, in the step of providing a system for orienting a surface of a stage which optionally has a sample having a surface supported thereupon, providing at least one selection from the group consisting of:
   a chopper or modulator in the beam path of said beam of electromagnetic radiation provided by said combination source and detector for providing a beam of electromagnetic radiation and detecting a portion thereof which reflects from said stage or sample surface, substantially along said arbitrary "N" axis;
   a chopper or modulator in the beam path of said beam of electromagnetic radiation provided by said source of electromagnetic radiation oriented to cause a beam of electromagnetic radiation to impinge on said surface of said stage or sample placed upon said stage, at an oblique angle of incidence with respect to said arbitrary "N" axis;
   a focusing means in the pathway of said beam of electromagnetic radiation caused to impinge on said surface of said stage or sample placed upon said stage, at an oblique angle of incidence with respect to said arbitrary "N" axis, prior to said stage;

a focusing means in the pathway of said specular reflected beam of electromagnetic radiation which is caused to impinge on said surface of said stage or sample placed upon said stage, at an oblique angle of incidence with respect to said arbitrary "N" axis, after said stage;

a polarization stage generator in the pathway of the beam provided by said source of electromagnetic radiation oriented to cause a beam of electromagnetic radiation to impinge on said surface of said stage or sample placed upon said stage, at an oblique angle of incidence with respect to said arbitrary "N" axis;

a polarization state analyzer in the pathway of the beam of electromagnetic beam provided by said source of electromagnetic radiation oriented to cause a beam of electromagnetic radiation to impinge on said surface of said stage or sample placed upon said stage at an oblique angle of incidence with respect to said arbitrary "N" axis, and is specularly reflected from said stage or sample surface.

18. A method of orienting a surface of a stage which optionally has a sample supported thereupon, comprising:

A) providing a system for orienting a surface of a stage which optionally has a sample having a surface supported thereupon, comprising:

a) a stage for supporting a sample, wherein said surface of said stage or sample is oriented such that a normal thereto projects substantially along an arbitrary "N" axis;

b) a source of electromagnetic radiation oriented to cause a beam of electromagnetic radiation to impinge on said surface of said stage or sample placed upon said stage, at an oblique angle of incidence with respect to said arbitrary "N" axis;

c) means for monitoring the height of said stage or sample placed upon said stage;

d) a specular beam detector of a specularly reflected electromagnetic beam which results from said oblique angle of incidence beam specularly reflecting from said surface of said stage or sample;

e) first rotation effecting means for causing said stage to rotate about axes which are substantially perpendicular to said arbitrary "N" axis;

f) said stage and first rotation effecting means for causing said stage to rotate being supported on translation means for moving said stage in a plane which is substantially perpendicular to said arbitrary "N" axis;

g) said translation means being supported on a second rotation effecting means for causing said stage to rotate about axes which are substantially perpendicular to said arbitrary "N" axis; and h) said system further comprising means for changing the relative distance between:

said source of electromagnetic radiation oriented to cause a beam of electromagnetic radiation to impinge on a surface of said stage or a sample placed on said stage, at an oblique angle of incidence with respect to said arbitrary "N" axis direction, and said stage;

substantially along the arbitrary "N" axis;

B) causing said source of a beam of electromagnetic radiation oriented to cause a beam of electromagnetic radiation to impinge on said surface of said stage or sample placed upon said stage, at an oblique angle of incidence to provide a beam of electromagnetic radiation, along an oblique angle of incidence to the surface of said stage or sample placed thereupon;

C) while monitoring the height of the surface of said stage or sample, causing said translation means for moving said stage in a plane which is substantially perpendicular to said arbitrary "N" axis to cause translation motion of said stage and if said specular beam detector output changes than then causing said first rotation means to cause rotation of said stage about said at least one of said axes which is substantially perpendicular to said arbitrary "N" axis and again causing said translation means for moving said stage in a plane which is substantially perpendicular to said arbitrary "N" axis to cause translation motion of said stage;

D) repeating step C if the output of said specular beam detector changes when said translation means for moving said stage in a plane which is substantially perpendicular to said arbitrary "N" axis causes is caused to effect translation motion of said stage and moving on to step E when said translation motion has substantially no effect on the output of said specular beam detector;

E) while monitoring the output of said specular beam detector of a specularly reflected electromagnetic beam which results from said oblique angle of incidence beam specularly reflecting from said surface of said stage or sample causing said second rotation effecting means for causing said stage to rotate substantially about at least one of said axes which is substantially perpendicular to said arbitrary "N" axis to a position which substantially maximizes the output of said specular beam detector;

said change in orientation or position of said stage or sample constituting a concrete and tangible change.

19. A method as in claim 18, wherein the means for monitoring the height of said stage or sample placed upon said stage comprises a focusing means between said source of electromagnetic radiation and said stage for supporting a sample, and a multi-element detector between said said stage for supporting a sample and said specular beam detector through which multi-element detector said reflected specular beam passes before entering said specular beam detector.

* * * * *